United States Patent [19]

Brownstein et al.

[11] Patent Number: 5,522,996

[45] Date of Patent: Jun. 4, 1996

[54] REMOVAL OF LITHIUM IONS FROM AQUEOUS SOLUTIONS

[75] Inventors: Sydney K. Brownstein, Lanark; Pierre-Yves Plouffe, Gloucester, both of Canada

[73] Assignee: National Research Council of Canada, Ottawa, Canada

[21] Appl. No.: 198,589

[22] Filed: Feb. 18, 1994

[51] Int. Cl.$^6$ .......................... B01D 15/04; B01D 71/60
[52] U.S. Cl. .......................... 210/638; 210/645; 210/681; 210/688; 210/912; 436/79
[58] Field of Search .................................. 210/638, 635, 210/656, 645, 646, 681, 912, 685, 688; 422/101; 424/78.01, 78.1, 78.17, 78.35, 78.36; 436/79; 514/183, 277

[56] References Cited

U.S. PATENT DOCUMENTS 4,959,135  9/1990  Zenner et al. ..................... 204/130

Primary Examiner—John Kim

[57] ABSTRACT

The invention disclosed relates to an agent capable of selectively binding lithium ions to form a lithium complex, employed in association with a biologically inert carrier or excipient. Typically, the agent is included in a novel graft polymer, such as a cross-linked polystyrene polymer. This invention may also be applied to sensing lithium ion concentrations in aqueous solution and to the selective removal of lithium ions from an aqueous solution, including biological fluids.

10 Claims, 2 Drawing Sheets

REMOVAL OF LITHIUM IONS FROM AQUEOUS SOLUTIONS

BACKGROUND OF THE INVENTION

1. Field of the Invention

This invention relates to a series of selective lithium chelators, e.g. ionophores, and to their uses.

Ionophores are complexing agents which are capable of reversibly binding ions. Such ion-selective materials can be used in sensors for the direct measurement of ions, in this case lithium ions. For example, the concentration of lithium ions in biological fluids such as blood, may be monitored. Also, the selectivity of these complexes for lithium ions can be used to selectively remove lithium ions from aqueous solutions including lithium and other metal cations, such as encountered in the recovery of pure lithium from its ores.

Lithium carbonate is typically used as an anti-manic drug. The main mechanism for excretion of excess lithium is through the kidneys. Unfortunately, in some patients this mechanism is not sufficient, resulting in an initial rise in lithium concentration to toxic levels. Moreover, since the therapeutic dosage (0.6–1.2 mmol/L) is close to toxic levels (1.5–2 mmol/L), lithium toxicity is common. Overdose symptoms include sluggishness, drowsiness, coarse tremors, vomiting, thirst, diarrhoea, blurred vision, confusion, increasing disorientation, seizures, and sometimes coma and death.

Moreover, since there is not much difference between therapeutic and toxic lithium levels it is desirable to name a simple and convenient method of monitoring lithium levels in the bloodstream. Lavage and activated charcoal (charcoal does not adsorb lithium effectively) can reduce lithium present in the gastrointestinal tract, but not the lithium present in the bloodstream. Since some patients have a low rhinal excretion rate for lithium, diuretics have limited use. Moreover, forced diuresis is a severe treatment which can disrupt the serum ion balance, and may cause infection.

Various methods are also known in the art for removing metal ions from aqueous solutions. For example, in Canadian Patent No. 1,221,499 of 5 May 1987 in the names of M. Corvette et. al., macroporous alkylaminophosphonic chelating resins are disclosed for removing calcium and magnesium from brines.

Also, in Canadian Patent no. 606,439 in the name of H. R. Lukens, metals other than alkali metals, may be usefully complexed with chelating polymers for stabilization of fuels. Specifically, by chelating the metal with a copolymer of a vinyl ester of a lower molecular weight alkyl carboxylic acid and an acyclic alpha-monoolefinic hydrocarbon.

A complex of the ligand $N(CH_2CH_2py)_3$, wherein py is 2-pyridyl, with copper ions, is known for example, from Synthesis and X-ray Structural Characterization of Cu(I) and Cu(II) Derivatives, K. D. Karlin et. al., Inorganica Chimica Acta. 64(1982) L219–L220.

A similar ligand i.e. $N(CH_2py)_3$, is known from Pyridine Derivatives, G. Anderegg and F. Wenk, Helvetica Chimica Acta. Vol. 50, Chapter 8 (1967)-No. 243, p. 2330–2332.

There is no teaching or suggestion in any of these references of the use of such ligands for selective removal of lithium ions from aqueous solutions, such as biological fluids e.g. gastro-intestinal fluids, blood and serum. It will also be appreciated from these references that the alkali metals, such as lithium have different complexing properties than other metals, and that there is no requirement for low toxicity in such environments.

At present, detection of $Li^+$ in aqueous solution involves AA, ICP, DCP or ion selective electrodes. Ion selective electrodes suffer from interference problems namely from $Na^+$, $K^+$ and $Ca^{+2}$. [Gadzepko. V. P. Y., et. al., Ion Selective Electrode Rev., 1986, 8, 173–207]. These interferences make ion selective electrodes for lithium, inadequate to the present, for application to biological fluids. The other methods, although more selective, are expensive and require bulky instruments.

SUMMARY OF THE INVENTION

According to one aspect of the Invention, a method for selectively removing lithium ions from an aqueous solution is provided comprising:

(a) contacting the solution with an agent capable of selectively binding lithium ions to form a lithium complex, said agent comprising a ligand of structural formula I or IA

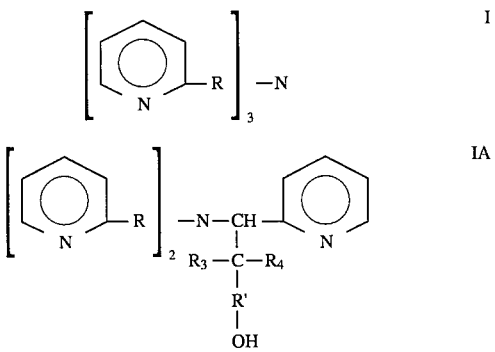

wherein R is lower-alkyl which may be the same or different, $R_3$ and $R_4$ are hydrogen, lower-alkyl or phenyl; R' if present is lower alkyl, and one or more of the pyridine rings may be substituted on the 3, 4, 5 or 6 positions, or a pharmaceutically acceptable salt thereof, in association with a biologically inert carrier or excipient, and (b) removing the complex, so formed.

As will be apparent hereinafter, when the aqueous solution is a biological fluid, the ligand is preferably included in a biologically inert polymer matrix, which may be in the form of beads. The ligand may also be usefully employed in association with conventional inert supports, such as silica gel.

According to another aspect of the Invention, a novel graft polymer of structural formula II

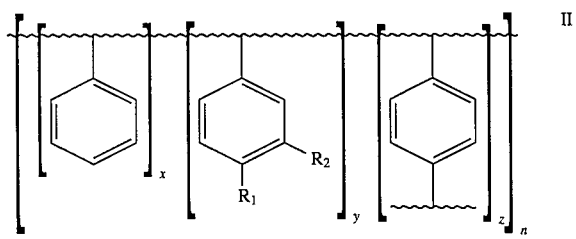

wherein
x=1–20,
y=1,
z=0–5,
n=30–200, one of $R_1$ and $R_2$ is H, the other being

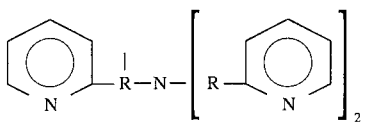

or

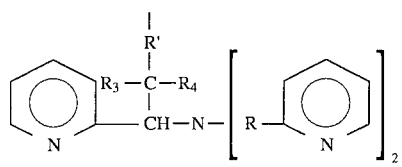

wherein $R_3$ and $R_4$=hydrogen, methyl or phenyl, R=lower-alkyl which may be the same or different, R' if present, is lower-alkyl, and one or more of the pyridine rings may be substituted at the 3, 4, 5 or 6 positions, and pharmaceutically acceptable salts thereof, is provided.

According to yet another embodiment of the invention, the ligands of molecular formula I or IA as defined above, may be used as active material in lithium ion-selective electrodes (ISEs'), for the direct determination of lithium in aqueous solutions, including biological fluids such as blood. As is well-known in the art, the signal from the ISE is monitored by a conventional high impedance millivoltmeter, such as an ACCUMET (trademark) 925 Microprocessor pH/mV/ISE Meter.

The term "lower alkyl" refers to a straight or branched chain saturated hydrocarbon group having from 1 to 4 carbon atoms e.g. methyl, ethyl, n-propyl, iso-propyl, n-butyl, iso-butyl, sec-butyl and tert-butyl.

The term "pharmaceutically acceptable salt" refers to salts that retain the desired biological activity of the parent compound and do not impart any undesired toxicological effects. Examples of such salts are; acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, fluconic acid, citric acid, malic acid, ascorbic acid, benzoic acid, tannic acid, pamoic acid, alginic acid, polyglutamic acid, naphthalenesulfonic acid, naphthalenedisulfonic acids, polygalacturonic acid.

It will be noted that when z is greater than zero, the polymer is cross-linked, and is known as a PS-DVB copolymer. Substituted polysulfones may also be used as the inert polymer matrix.

BRIEF DESCRIPTION OF THE ACCOMPANYING DRAWING

DETAILED DESCRIPTION OF THE PREFERRED EMBODIMENTS

Figure 1:
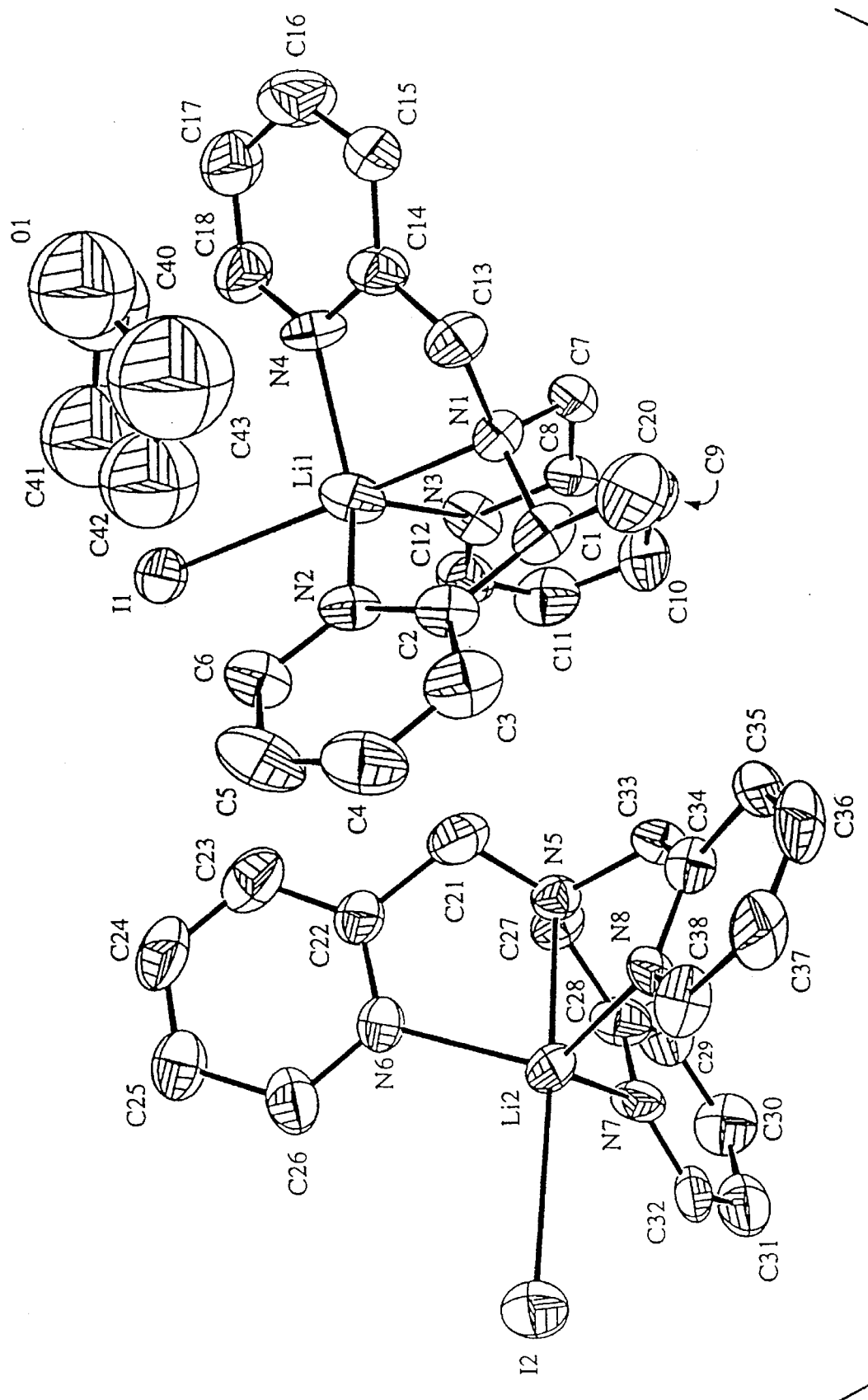
FIG. 1 is a perspective drawing of the crystal structure of an asymmetric unit which includes two lithium chelates, formed according to the invention.

It has been found that a ligand of formula I or IA as defined above selectively complexes with lithium, without undue disturbance of the concentrations of other metallic cations, including sodium and potassium, normally present in biological fluids.

In a preferred embodiment of the invention, the ligand of formula I or IA is included in a graft polymer of formula II as defined above.

For biological use, the ligand is chemically bound to a polymer, either directly or through a spacer group, to obtain a graft polymer which is insoluble in body fluids and biologically inert and which still retains its ability to selectively complex/chelate lithium ions. The graft polymer may be ingested orally (or parenterally) or used in a dialysis apparatus. If the graft polymer is ingested orally in order to selectively remove lithium via the digestive tract, it would do so in the intestines and be excreted. However, if it is used to remove lithium in a dialysis procedure, it could be regenerated easily by an acid wash, and the columns used again.

The graft polymers are prepared by the addition of a ligand of formula I or IA, highly specific for lithium chelation, to a polymer which is insoluble and inert in body fluids. Specific examples of appropriate ligands of formula I are tris (2-pyridyl) amines in which the link of the amine to the pyridine ring is through a lower alkyl group, and where there may be substituents on the 3, 4, 5 or 6 position of one or more of the pyridine rings. The compounds of formula IA are novel compounds and may also be represented by the following structure:

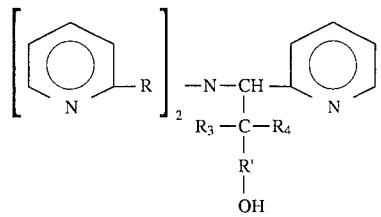

One specific example of such compounds, i.e. when R is methylene, $R_3$ and $R_4$ are methyl and R' is not present, is bis [(2-pyridyl)methyl]-1-[1-(2-pyridyl)-2-methyl propane-2-ol] amine. Other examples are higher lower-alkane homologs in which R is methylene, $R_3$ and $R_4$ are methyl and R' is lower-alkyl. It is noted that the carbon β to the amino nitrogen is hydrogen-free.

Examples of a polymer are linear or cross-linked polystyrenes substituted, in part, in the meta or para position by a chloromethyl group. This chloromethyl group may then be partially or completely reacted with a lithiated derivative of the chelating ligand to give the graft polymer. Other examples of a polymer are linear or cross-linked polysulfones substituted, in part, in the ortho position by a lithium atom. This lithium atom may then be reacted with a chlorinated derivative of the chelating ligand to give the graft polymer.

It will also be appreciated that the ligand of formula I may be covalently bonded to the surface of a conventional biologically inert support e.g. silica gel or otherwise attached to biologically inert polymeric beads, as described for example, in the above mentioned Canadian patent no. 1,221,499.

EXPERIMENTAL (Synthesis and Characterization of Ligands and Complexes)

Structures of a Li-Ligand Complex

The x-ray diffraction data were collected at −120° C. on a Rigaku diffractometer with MoKα radiation using the omega-2 theta scan technique to a maximum 2 theta value of 50°.

The structure was solved by direct methods. All the atoms were refined anisotropically except the solvent molecule and the hydrogens. The hydrogen atoms are in calculated positions. The final cycle of full matrix least-squares refinement was based on 4208 observed reflections (I>2.5 sigma(I)) and 463 variable parameters. Weights based on counting statistics were used.

There are 2 chelate molecules per asymmetric unit. The difference between the 2 molecules is the presence of a methyl group in one of the molecules. There is also a molecule of the solvent, tetrahydrofuran, in the unit cell.

All the calculations were performed using the NRCVAX crystallographic software package (1). The crystal data are listed in Table I, and the structure is shown in FIG. I.

TABLE I

Crystallographic Data for $Li_2(CH_2NC_5H_4)_3N$ $(CHCH_3NC_5H_4)(CH_2NC_5H_4)_2NI_2 \cdot THF$

| | |
|---|---|
| chemical formula: | $C_{41}H_{46}N_8Li_2I_2O$ |
| space group: | $P2_1/c$ |
| a = 13.077(4)Å | T = −120° C. |
| b = 12.221(11)Å | λ = 0.70930Å |
| c = 26.613(7)Å | pcalcd = 1.464 g cm$^{-3}$ |
| β = 94.642 (24) deg | μ(MoKα) = 15.1 cm$^{-1}$ |
| | R = 0.094 |
| V = 4239(4)Å$^{-3}$ | Rw = 0.083 |
| Z = 4 | |
| fw = 934.55 | |

In order to understand the ligand-Lithium bonding, Ab initio calculations for the model compound $LiN(CH_2CHNH_2)_3$ were performed using the program GAMESS[2] and the electronic properties were examined with natural orbital analysis[3]. The extended 6-31G* basis sets[4] were used for all of the heavy atoms. The geometry optimization was performed with full analytical gradient $C_{3v}$ symmetry.

The energetics and dynamics of Lithium and Sodium complex formation were determined by high resolution nuclear magnetic resonance spectroscopy. All magnetic resonance spectra were obtained with a Bruker AM 400 spectrometer operating at a proton frequency of 400.13 MHz. Spectra were normally obtained at room temperature in either deuteroacetone, deuterochloroform or deuterated water as solvent. Assignments are as follows: s for singlet, br for broad.

Lifetimes for exchange were obtained by matching experimental spectra with theoretical ones calculated for particular lifetimes and chemical shifts using a stochastic procedure [5]. From the temperature dependence of the rate constants, an enthalpy of formation of 8.0 kCal mole$^{-1}$ was found for the Li complex and 3.0 kCal mole$^{-1}$ estimated for the Na complex. This corresponds to a selectivity of approximately 10,000 to one.

All syntheses were performed under nitrogen in appropriately sized three-neck flasks. Tetrahydrofuran (THF) was distilled over sodium/benzophenone under nitrogen just before use. The complex tris (2-pyridyl)methyl) amine (TMPA) was prepared by the method of Anderegg and Wenk [6]. The complex tris (2-(2-pyridyl)ethyl)amine(TEPA) was prepared based on a partial preparation reported from Karlin et. al.[7]. Solvents and liquid reagents were transferred by means of an appropriately sized glass syringe. The compound 2-picoline chloride hydrochloride was purchased from Aldrich and recrystallized from hot acetone before use.

Vinyl pyridine, 2-methylpyridinoamine, methyllithium and methyl iodide were purchased from Aldrich and used as received.

Ultraviolet spectra were recorded in water on a Varian Cary 210 via auxiliary computer control. Melting points were measured in sealed tubes on a Gallenkamp melting point apparatus, and are uncorrected.

Electrospray experiments were performed on an atmospheric-pressure ionization triple quadrupole mass spectrometer (SCIX, TAGA, Model 6000E), which has an upper m/z limit of approximately 1400. For electrospray studies, the corona discharge assembly was removed and replaced with a laboratory-built electrospray probe, which was fabricated from a 3 cm long capillary stainless steel tube (Hamilton, 33-gauge, ~100 μm i.d.) previously attached to an approximately 5 cm×⅟₁₆" OD stainless steel tube (typically used in gas chromatography). The probe tip was electropolished prior to use. The optimum probe tip position was established from time to time, but was generally found to be about 1–2 cm from the interface plate with the spray off-axis from the orifice. Polarization of the spray probe was achieved via a 50 MΩ current-limiting resistor in series with a high-voltage power supply (Tennelec, Model TC950) set typically at 2.5–3.5 kV. The electrospray current was monitored by a laboratory-built microammeter that could be floated above ground; typical values were between 0.1 and 0.2 μA.

The sample solutions were continuously infused into the spray probe by means of a syringe pump (Harvard Apparatus, Model 22) at a typical flow rate of 20 μl/min.

Electrical isolation of the pump from the probe was achieved by using polytetrafluoroethylene (Teflon) connection tubing.

The lens and quadrupole voltages were optimized for electrospray. Mass spectra were acquired with a typical measurement time of 50 ms per m/z unit at unit mass resolution or better [8].

Preparation of Tris ((2-pyridyl)methyl) amine (TMPA)

Based on Anderegg and Wenk's preparation referred above, a solution of 2-picoline chloride hydrochloride (13 g, 79 mmole) in water (5 mL) was prepared in a 500 mL three neck flask and cooled to 0° C. in an ice bath. To that solution, sodium hydroxide (14.7 mL, 79.4 mmole, 5.4N (i.e. 20% wt)) was slowly added to give a pink emulsion. To this emulsion, 2-methylpyridino-amine (4.27 mL, 39.5 mmole) was slowly added. During the next 4 days, the pH was maintained between 9.5 and 11 by adding sodium hydroxide (5.4N). About 12.6 mL (68 mmole) of NaOH was required. A solution of perchloric acid (24 mL, 120 mmole, 5.0N) was added and brown crystals started to form. After 6 hrs., a hot (80° C.) saturated solution (100 mL) of sodium perchlorate was added. After 2 hrs. of further crystallisation, the solution was filtered. The wet crystals were immediately dissolved in sodium hydroxide (200 mL, 5.4N) and repeatedly extracted with diethyl ether (40×50 mL). The extract was dried with magnesium sulfate, filtered through paper and evaporated to dryness under reduced pressure. Recrystallization from diethyl ether gave the product as light beige crystals (5.66 g, 19.5 mmole, 49.3%). M.P.: 80°–83° C. UV: $\lambda_{max}$=263 nM; ε=11300 M$^{-1}$ cm$^{-1}$. Electro Spray Mass Spectrometry: 291.3 m/z. The structure is illustrated in FIG. 1A.

Preparation of Tris (2-(2-pyridyl)ethyl) amine (TEPA)

Based on Karlin et. al.'s partial preparation referenced above, a solution of ammonium acetate (4.00 g, 51.9 mmole)

in methanol (100 mL) was prepared in a 250 mL three neck flask fitted with a condenser. To that solution, vinyl pyridine (60 mL, 556.4 mmole) was added. The mixture was brought to reflux and maintained for 8 days. After that time, the solution was reduced to dryness under vacuum. The residue was extracted with toluene and dried with magnesium sulfate and reduced to dryness under vacuum. The residue was dissolved in the minimum of diethyl ether and chromatographed over activated alumina (20 mm×250 mm) and eluted with diethyl ether. The brown band was collected and the eluent was changed to 20% (v/v) methanol in diethyl ether thereby eluting a red band. Both bands were reduced to dryness under vacuum to give golden oil for band 1 (TEPA, 6.96 g, 20.96 mmole, 11%) and a dark red oil for band 2 (bis (2-(2-pyridyl)ethyl) amine, BEPA, 0.58 g, 2.56 mmole, 4.9%). UV: $\lambda_{max}$=261 nM; $\epsilon$=1025 $M^{-1}$ $cm^{-1}$. Electro Spray Mass Spectrometry of TEPA: 334 m/z.

Preparation of Tris (2-(2-pyridyl)ethyl) amine Tetra Hydrochloride (TEPA○4HCl)

The compound TEPA (7.8 g, 23 mmole) was dissolved in 9N HCl (20 mL). To this solution, ethanol (300 mL) was slowly added. The powder was filtered and washed with ethanol and air dried for 1 hr. The yield was quantitative. M.P. 213°–215° C. Elemental analysis: Calc.52.74% C; 5.90% H; 11.71% N; 29.7% Cl. Found 51.90% C; 5.69% H; 11.16% N; 29.8% Cl. UV: $\lambda_{max}$=261 nM; $\epsilon$=1260 $M^{-1}$ $cm^{-1}$.

Preparation of Bis [(2-pyridyl)methyl]-1-[(2-pyridyl)ethyl]amine (TMPA-Me)

The complex TMPA (0.23 g, 0.79 mole) was dissolved in THF (5 mL) and cooled to −78° C. in an ethanol/dry ice bath. To the cooled solution, methyllithium (0.56 mL, 1.4M in ether, 0.79 mmole) was added dropwise. After stirring for 5 minutes, methyl iodide (0.60 mL, 9.6 mmole) was added dropwise and stirred for 10 minutes. The product was warmed to room temperature and stirred for 1 hr. Upon exposure to air, the residual pink colour disappeared. The solution was reduced to dryness and extracted with $CH_2Cl_2$ and filtered. The yellow filtrate was collected and hexanes was added until turbid. Crystallographic grade crystal (0.2126 g) were collected and dried under vacuum. X-ray crystallography indicates a 1:1:1 crystal of desired product, TMPA and THF. Therefore, the yield is 0.23 mmole (29%) as a mixture with 0.23 mmole (29%) TMPA and THF. M. P. 211°–218° C. The structure is illustrated in FIG. 1B.

Sequential Preparation of Bis [(2-pyridyl)methyl]-1-[1-(2-pyridyl)-2-methyl-propane-2-ol] amine Step A. Preparation of 1-(2-pyridyl)-2-methyl-propane-2-ol ($PyCH_2C(OH)(CH_3)_2$).

A solution of 2-picoline (1.58 ml, 16.0 mmole) in THF (10 ml) was prepared and cooled to −78° C. in an ethanol/dry ice bath. To that solution, butyllithium (10 ml of 1.6M, 16.0 mmole) was added dropwise. The resulting orange slurry was stirred for 30 min. Acetone (1.17 ml, 16.0 mmole) was slowly added. The dry ice bath was removed and the solution was stirred for 30 min. until room temperature was reached. The colourless solution was stirred vigorously while water (0.30 ml, 16.7 mmole) was added. The solution was filtered through celite (1 cm) and the solvent was then removed by distillation under vacuum until a golden oil was obtained. The oil was transferred to a U-tube and the remainder of the solvent was trap-to-trap distilled for 1 hour from room temperature to liquid nitrogen with stirring.

yield: 1.11 g (7.34 mmole, 46%)

NMR 1.23 (6H, C$\underline{H}_3$), 2.92, (2H, C$\underline{H}_2$), 5.84 (1H, O$\underline{H}$), 7,16 (2H, Py (positions 3 and 5), 7,62 (1H, Py (position 4)), 8.47 (1H, Py (position 6)).

Step B. Preparation of (1-bromo)-1-(2-pyridyl)-2-methylpropane-2-ol

The compound $PyCH_2C(OH)(CH_3)_2$ (0.50 g, 3.31 mMole from step A was mixed with N-bromosuccinimide (0.78 g, 4.38 mMole) and benzoyl peroxide (0.040 g, 0.17 mMole) in a 150 mL 1-neck round bottom flask. Carbon tetrachloride (60 mL) was added and the reaction flask was fitted with a water condenser. The solution was brought to reflux for 3.5 hrs. After cooling to 0° C., the solid residues were filtered and washed with $CCl_4$ (3×5 mL). The washes were combined with the mother liquor and the solvent was reduced under vacuum to give a yellow oil (1.07 g, 0.76 g prod.+0.31 g $CCl_4$, 90% pure by NMR with 10% $PyCH_2C(OH)(CH_3)_2$).

NMR: 1.25 (s, 3H, CH3), 1.49 (s, 3H, CH3), 4.99 (s, 1H, CH), 6.2 (br, OH)

Step C. Preparation of 1-phthalamido-1-(2-pyridyl)-2-methyl-propane-2-ol (Semi-micro scale)

The oil from Step B was redissolved in dry dimethylformamide (40 mL) and potassium phthalimide (0.61 g, 3.31 mMole) was added. The solution was refluxed for 15 min. and then reduced to dryness. The resulting paste was redissolved in $CHCl_3$ and filtered. The mother liquor was reduced under vacuum to give a brown oil (0.80 g, 3.0 mMole, ~75% yield contaminated with $PyCH_2C(OH)(CH_3)_2$ and DMF).

NMR: 1.12 (s,3H, CH3), 1.53 (s, 3H, CH3), 4.01 (s, 1H, CH)), 6.2 (br, OH).

Step D. (Preparation of 1-amino-1-(2-pyridyl)-2-methylpropane-2-ol (Semi-micro scale)

The product obtained in Step C as the PyCH(Phth)C(OH)(CH$_3$)$_2$ was dissolved in 2 mL methanol, 2 mL THF and 1 mL hydrazine (1:1 with water) and left for four days. After this time, a few drops of conc. HCl was added and the solution was filtered. The filtrate was mixed with NaOH (2 mL, 1N) and extracted with $CH_2Cl_2$. The organic layer was evaporated to dryness and extracted with $CDCl_3$ for NMR. NMR showed ⅔ desired product and ⅓ $PyCH_2C(OH)(CH_3)_2$ and other decomposition products.

NMR: 1.44 (s, 3H, CH3), 1.67 (s, 3H, CH3), 4.77 (s, 1H, CH), 5.8 (br, OH).

Step E Preparation of $PyCH[N(CH_2Py)_2]C(OH)(CH_3)_2$ (NMR scale)

In the NMR tube used to characterize the compound $PyCH(NH_2)C(OH)(CH_3)_2$, was added excess 2-picolyl chloride hydrochloride and some NaOH (1N) until a pink colour persisted. After 24 hr of stirring, the organic layer was removed, dried through anhydrous Mg(SO$_4$)$_2$ and the NMR was taken. It is that of the product.

NMR: 1.12 (s, ~3H, CH3), 1.53 (s, ~3H, CH3), 3.98 (s, ~1H, CH)), 4.68 (br, OH)

The magnetic resonance parameters for some of these compounds are listed in Table II.

TABLE II

$^1$H NMR data for TMPA, TMPA-Me, TEPA and DEPA.[a]

| | NH | CH$_3$ | CH$_2$ | Py |
|---|---|---|---|---|
| TMPA | | | 3.883[b,c] | 7.14(H$_\beta$)[d,e] |
| | | | | 7.59(H$_\delta$)[d,e] |
| | | | | 7.66(H$_\gamma$)[d,e] |
| | | | | 8.56(H$_\alpha$)[d,e] |
| TMPA-Me | | 1.583[e,f,g] | 3.658(CH$_2$H$_b$)[f,h,i] | 7.21(H$_\delta$, H$_{\delta'}$, H$_\beta$, H$_{\beta'}$)[c,d] |
| | | | 3.767(CH$_2$H$_d$)[f,i,j] | 7.13(H$_\gamma$)[d,j] |
| | | | 3.807(CH$_2$H$_d$)[f,i,j] | 7.65(H$_\gamma$)[d,l] |
| | | | 3.925(CHM$_e$)[g,i,k] | 9.38(H$_\alpha$)[d,l] |
| | | | 4.070(CH$_2$H$_b$)[f,h,j] | 9.44(H$_\alpha$)[d,j] |
| TEPA | | | 2.905(CH$_2^\Phi$)[c,d] | 7.00(H$_\delta$)[d,e] |
| | | | 2.985(CH$_2^\Psi$)[c,d] | 7.09(H$_\beta$)[d,e] |
| | | | | 7.52(H$_\gamma$)[d,e] |
| | | | | 8.52(H$_\alpha$)[d,e] |
| TEPA o 4HCl[o] | | | 3.713(CH$_2^\Phi$)[c,d] | 8.03(H$_\beta$)[d,e] |
| | | | 3.930(CH$_2^\Psi$)[c,d] | 8.10(H$_\delta$)[d,e] |
| | | | | 8.61(H$_\gamma$)[d,e] |
| | | | | 8.78(H$_\alpha$)[d,e] |
| BEPA | 2.28[j,m] | | 2.978[d,n] | 7.12(H$_\beta$)[d,l] |
| | | | 3.042[d,n] | 7.15(H$_\delta$)[d,i] |
| | | | | 7.58(H$_\gamma$)[d,l] |
| | | | | 8.49(H$_\alpha$)[d,l] |

[a]in CDCl$_3$: reported in PPM relative to TMS as internal reference;
[b]singlet;
[c]6H;
[d]multiplet;
[e]3H;
[f]doublet;
[g]$J_{H-H}$ = 7.04 Hz;
[h]$J_{H-H}$ = 15.26 Hz;
[i]$J_{H-H}$ = 15.85 Hz;
[j]1H;
[k]quartet;
[l]2H;
[m]broad;
[n]4H;
[o]in D$_2$O: reported in PPM relative to DSS.

RESULTS

A synthesis was attempted to put a methyl group in place of a hydrogen on one of the CH$_2$ groups of TMPA. Crystals were obtained containing equal quantities of TMPA and methylated TMPA, both complexed to a lithium cation with iodide as the counter ion. All bond distances and angles are normal. The three pyridyl nitrogens form a plane. The Li atoms lie 0.39 Å from the planes away from the amino nitrogen. Within 3 sigma there is no significant difference in the nitrogen-lithium bond lengths. These are essentially the same length as was found for the adducts of other lithium chloride, pyridine complexes, 2.05 to 2.16 Å.[9].

Preparation of the Polymer PS-TMPAMS

The reaction was performed under an inert atmosphere of dry nitrogen using standard Schlenk technique. In a three neck round bottom flask (150 mL), the ligand TMPA (1.50 g, 5.20 mmole) was dissolved in THF (20 mL) and cooled to −78° C. in an ethanol/dry ice bath. To this solution, butyl lithium (8.25 mL, 1.6N in hexanes, 13.2 mmole) was added dropwise. The temperature was allowed to rise to room temperature by removing the dry ice bath. In a separate three neck flask (150 mL), the polymer (polystyrene-chloromethyl styrene, 1:3, Mw=38 000, 2.46 g, 5.2 mmole Cl) was dissolved in THF (50 mL). The polymer was added to the lithiated ligand dropwise via canula. The solution was brought up to reflux and maintained for 24 hrs. using a heating mantle. The resulting polymer was exposed to air and purified by filtering through a course frit filter and precipitating the filtrate into methanol (500 mL). The polymer was recovered by filtration and air dried for 2 hrs and further dried under vacuum overnight. Yield: 1.01 g, NMR: 8.55(3H,Py), 5.90–8.00 (108H, Py+Ar), 2.88 (7 benzylic CH+CH$_2$), 0.90–2.30 (45H, aliphatic CH+CH$_2$).

Test Protocol for Removal of Li$^+$ by Column

Dry polymer (0.4435 g) was placed in a disposable pipette plugged with glass wool. The top of the column was also plugged with glass wool. Ethanol (95%, 2 mL) was eluted over the dry column. The flow was stopped and the column was allowed to stand overnight. The column was then washed with HCl (3N, 5 mL) followed by distilled and deionized water (20 mL) until the effluent was neutral to pH paper. The dead volume of the column was measured to be 1 mL. A solution of LiI (0.61 ppm, 2 mL) was passed over the column. The eluent was changed to water (8 mL) followed by HCl (3N, 6 mL). The effluent was collected in 1 mL aliquots and analyzed in house by flame atomic absorption. The results are shown in FIG. 2.

Results for Removal of Li$^+$ by Column

Figure 2:
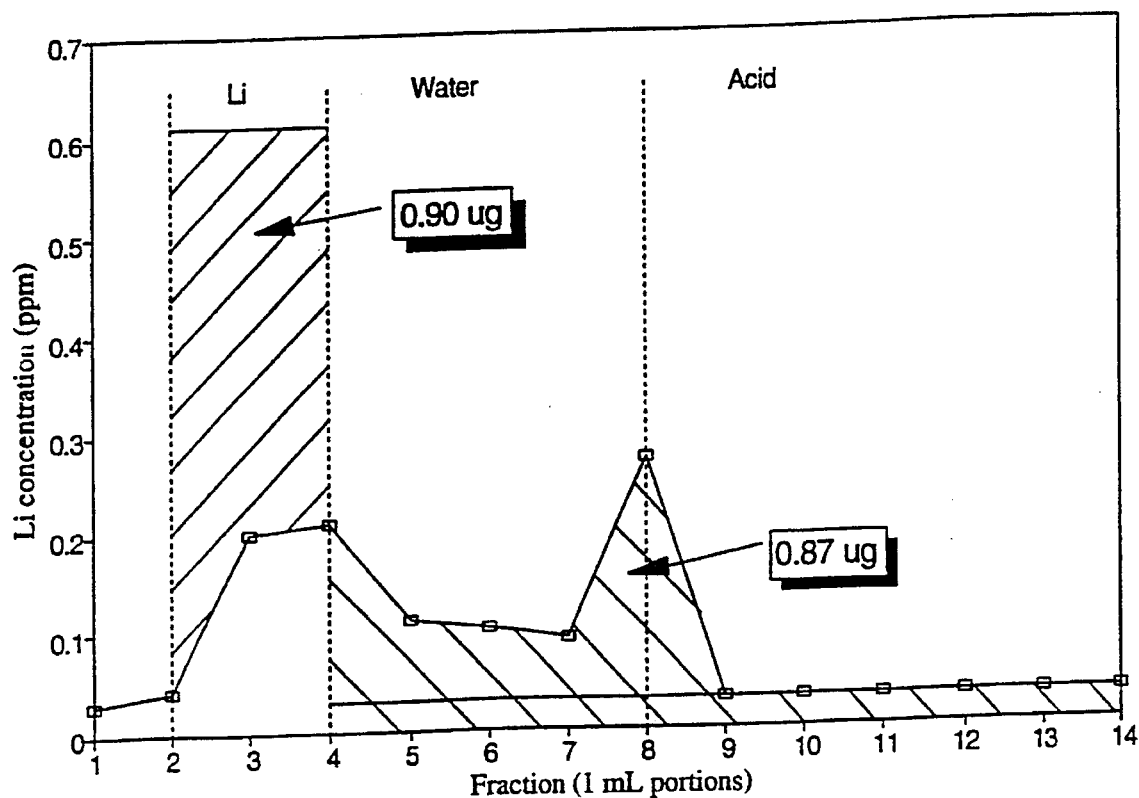
FIG. 2 is a graph illustrating the removal of lithium ions from an aqueous solution by a graft polymer including a complexing ligand according to the invention.

As seen in FIG. 2, fractions 2 to 4 are the Li$^+$ loading step. The shaded area above the curve (effluent concentration) and below the line (influent concentration) corresponds to the amount of Li$^+$ absorbed by the column (i.e. 0.90 µg). The fractions 4 to 8 correspond to the water wash. In this region, the shaded area below the curve corresponds to the amount of Li$^+$ which has been washed out. Therefore, the area under the curve from fraction 4 to 14 is the total amount of $Li^+$ recovered after loading (i.e. 0.87 µg).

The results indicate that $Li^+$ can be removed from water using the polymer and then recovered from the said polymer using a distilled water wash, or preferably, using an acid wash.

TOXICOLOGY

The active agent and/or pharmaceutically acceptable salts thereof can be converted in a known manner into the customary formulations such as tablets, dragees, pills, granules, aerosols, syrups, emulsions, suspensions and solutions, using inert-non-toxic, pharmaceutically acceptable ajuvants, carriers, excipients or solvents. The therapeutically active agent should in each case be present here in a concentration of about 0.5 to 90% by weight of the total mixture, that is to say in amounts which suffice to achieve the dosage range, hereinafter indicated.

The formulations are prepared, for example, by extending the active agent with solvents and/or excipients, optionally with the use of emulsifiers and/or dispersing agents, and for example, when using water as a diluent, organic solvents can optionally be used as auxiliary solvents.

Examples of auxiliary substances which may be mentioned are: water, non-toxic organic solvents, such as paraffins (for example groundnut oil/sesame oil), alcohols (for example ethyl alcohol and glycerol), excipients, such as, for example, ground natural minerals (for example kaolins, aluminas, talc and chalk), ground synthetic minerals (for example highly disperse silica and silicates) and sugars (for example sucrose, lactose and glucose), emulsifiers (for example polyoxyethylene fatty acid esters, polyoxyethylene fatty alcohol ethers, alkyl-sulphonates and arylsulphonates), dispersants (for example Lignin, sulphite waste Liquors, methylcellulose, starch and polyvinylpyrrole) and Lubricants (for example magnesium stearate, talc, stearic acid and sodium sulphate).

For therapeutic use the active agent is preferably included in a graft polymer of formula II as defined above. Administration is effected in the customary manner, preferably orally or parenterally, particularly prelingually or intravenously. In the case of oral use, the formulations can, of course, also contain, in addition to the excipients mentioned, additives such as sodium citrate, calcium carbonate and dicalcium phosphate, together with various additional substances, such as starch preferably potato starch, gelatine and the like. Furthermore, Lubricants, such as magnesium stearate, sodium lauryl sulphate and talc, can be used concomitantly when making tablets. In the case of aqueous suspensions, the graft polymer can be mixed with various flavour-improving agents or colorants in addition to the above-mentioned auxiliary substances.

In the case of parenteral use, solutions of the graft polymer, using suitable liquid excipients, can be employed.

However, when orally administered in association With a graft polymer, the therapeutically effective dosage including the graft polymer is 0.1 to 0.5 g/kg, preferably about 0.5 g/kg, of body weight.

Nevertheless, it may be necessary, under certain circumstances, to deviate from the amounts mentioned, and in particular to do so as a function of the body weight or of the nature of the administration method, of the individual behaviour towards the medicament, the nature of its formulation, and the time or interval over which the administration takes place. Thus, it can in some cases be sufficient to manage with less than the above-mentioned minimum amount, whereas in other cases the upper limit mentioned may be exceeded. In the case of administration of larger amounts, it may be advisable to divide these into several individual administrations over the course of the day.

REFERENCES

1. Gabe, E. J., Lee, F. L., LePage, Y., J., Appl. Crystallogr. 22, (1989) 384.
2. Dupuis, M., Sprangler, D. and Wendoloski, J. J., National Resource for Computations in Chemistry, Software Catalog, Program QG01, University of California, Berkeley (1980); The version of GAMESS is described in, Schmidt, M. W., Baldridge, K. K., Boatz, J. A., Jensen, J. H., Koseki, S., Gordon, M. S., Nguyen, K. A., Windus, T. L., Elbert, S. T., QCPE Bulletin, 10, (1990) 52.
3. Reed, A. E. and Weinhold, F., J. Chem. Phys., 78 (1983) 4066; Reed, A. E. and Weinhold, F., J. Chem. Phys., 83 (1985) 735.
4. Hariharan, P. C. and Pople, J. A., Theoret. Chim. Acta 28, 213 (1973).
5. Brownstein, S., Bornais, J., Can. J. Chem. 46 (1968) 225–228.
6. Anderegg, G., Wenk, F., *Helvetica Chimica Acta*, 50, 243 (1967), 2330–2332.
7. Karlin, K. D., Hayes, J. C., Hutchinson, J. P., Hyde, J. R., Zubieta, J., *Inorganica Chimica Acta*, 64 (1982), L219–L220.
8. Le Blanc, J. C. Y., Beuchemin, D., Siu, K. W. M., Guevremont, R., Berman, S. S., *Org. Mass Spectrom.*, 26 (1991), 831–839.
9. Durant, F., Pinet, P., Van Meersche, M., Acta Cryst. 22, (1967) 52–57.

We claim:

1. A method for selectively removing lithium ions from an aqueous solution, comprising contacting the solution with an agent capable of selectively binding lithium ions to form a lithium complex, said agent comprising a ligand of molecular formula I or IA

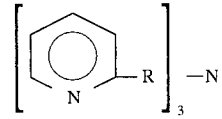

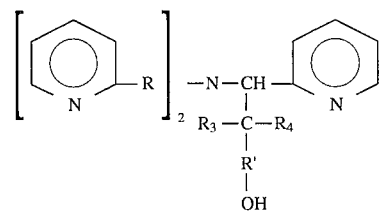

wherein R is lower-alkyl, $R_3$ and $R_4$ are hydrogen, lower-alkyl or phenyl; R' if present is lower-alkyl, and one or more of the pyridine rings may be substituted at the 3, 4, 5 or 6 positions, or a pharmaceutically acceptable salt thereof, in association with a biologically inert carrier or excipient, and (b) removing the complex, so formed.

2. A method according to claim 1, wherein the ligand of formula I or formula IA as defined in claim 1, is included in a biologically inert graft polymer of formula II

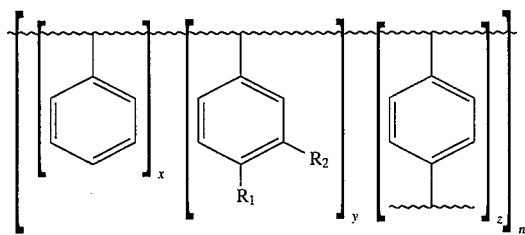

wherein
x=1–20
y=1,
z=0–5,
n=30–200,
one of $R_1$ and $R_2$ is H, the other being

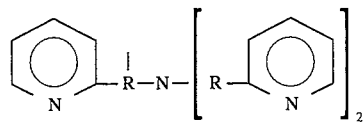

or

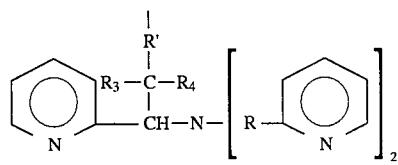

wherein $R_3$ and $R_4$=hydrogen, methyl or phenyl, R=lower-alkyl if present R'=lower-alkyl, and one or more of the pyridine rings may be substituted at the 3, 4, 5 or 6 positions, or a pharmaceutically acceptable salt thereof.

3. A method according to claim 2, wherein the polymer of formula II is a polymer containing repeat units in which $R_1$ is H and $R_2$ is

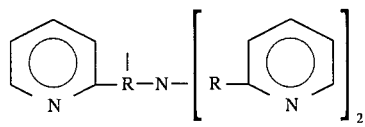

and repeat units in which $R_2$ is H and $R_1$ is

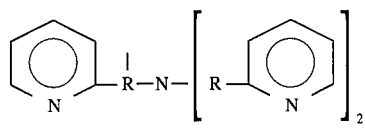

wherein R is lower-alkyl.

4. A method according to claim 3, wherein R is methyl or ethyl.

5. A method according to claim 4, wherein Z=0 and X is 2.

6. A method according to claim 2, wherein the lithium ions are removed from an aqueous solution by dialysis with a graft polymer of formula II, and including the additional step of applying an acid wash to remove the lithium ions to regenerate the polymer of formula II.

7. A method according to claim 6, wherein the aqueous solution is a biological fluid.

8. A method according to claim 7, wherein the biological fluid is selected from the group consisting of blood and serum.

9. A method according to claim 2, wherein a therapeutically effective amount of the polymer of formula II is orally ingested by a patient in need of such treatment in order to selectively remove lithium ions via the digestive tract.

10. A method according to claim 9, wherein the therapeutically effective amount is about 0.5 g/kg of patient body weight.

* * * * *